United States Patent
Zhu et al.

(10) Patent No.: US 12,264,121 B2
(45) Date of Patent: Apr. 1, 2025

(54) 1,3-BISISOCYANATOMETHYLCYCLOHEXANE COMPOSITION AND OPTICAL RESIN PREPARED THEREFROM

(71) Applicant: WANHUA CHEMICAL GROUP CO., LTD., Shandong (CN)

(72) Inventors: Fulin Zhu, Shandong (CN); Jianfeng Li, Shandong (CN); Peng Wang, Shandong (CN); Wenbin Li, Shandong (CN); Jie Chen, Shandong (CN); Qiao Wang, Shandong (CN); Qian Wu, Shandong (CN); Hao Chen, Shandong (CN); Yonghua Shang, Shandong (CN); Yuan Li, Shandong (CN)

(73) Assignee: WANHUA CHEMICAL GROUP CO., LTD., Shandong (CN)

( * ) Notice: Subject to any disclaimer, the term of this patent is extended or adjusted under 35 U.S.C. 154(b) by 430 days.

(21) Appl. No.: 17/772,352

(22) PCT Filed: Jul. 7, 2020

(86) PCT No.: PCT/CN2020/100732
§ 371 (c)(1),
(2) Date: Apr. 27, 2022

(87) PCT Pub. No.: WO2021/103550
PCT Pub. Date: Jun. 3, 2021

(65) Prior Publication Data
US 2022/0402865 A1    Dec. 22, 2022

(30) Foreign Application Priority Data

Nov. 29, 2019  (CN) .......................... 201911199670.X

(51) Int. Cl.
*C07C 265/14*   (2006.01)
*C08G 18/38*    (2006.01)
(Continued)

(52) U.S. Cl.
CPC ........ *C07C 265/14* (2013.01); *C08G 18/3855* (2013.01); *C08G 18/757* (2013.01); *G02B 1/041* (2013.01)

(58) Field of Classification Search
CPC .................................................... C07C 265/14
See application file for complete search history.

(56) References Cited

U.S. PATENT DOCUMENTS 4,443,597 A    4/1984  Kamatani et al.
4,565,835 A    1/1986  Oertel et al.
(Continued)

FOREIGN PATENT DOCUMENTS

CA    2504166    5/2004
CN    1517336    8/2004
(Continued)

OTHER PUBLICATIONS

Japanese Office Action with English Translation issued for Application No. 2022-524141, mailed Apr. 14, 2023.
(Continued)

*Primary Examiner* — Michael L Leonard
(74) *Attorney, Agent, or Firm* — Barnes & Thornburg LLP

(57) ABSTRACT

Disclosed is a 1,3-bisisocyanatomethylcyclohexane composition and an optical resin prepared therefrom. The composition comprises, based on the weight of 1,3-bisisocyanatomethylcyclohexane, a) 65%-95 wt % of trans-1,3-bisisocyanatomethylcyclohexane; b) greater than 0 and less than or equal to 0.5 wt %, preferably 0.02-0.5 wt % of 1,4-bisisocyanatomethylcyclohexane. Preferably, the 1,3-bisisocyanatomethylcyclohexane composition contains greater than 0 and less than or equal to 600 ppm of 1-isocyanatomethyl-3-methylcyclohexane, based on the weight of 1,3-bisisocyanatomethylcyclohexane. The 1,3-
(Continued)

bisisocyanatomethylcyclohexane composition is used for preparing an optical resin, which can be applied to produce an optical lens with a better performance in preventing opacification and optical distortion.

11 Claims, 1 Drawing Sheet

(51) Int. Cl.
*C08G 18/75* (2006.01)
*G02B 1/04* (2006.01)

(56) References Cited

U.S. PATENT DOCUMENTS

| | | | | |
|---|---|---|---|---|
| 5,086,150 | A * | 2/1992 | Frauendorf | C08G 18/4238 521/137 |
| 6,008,296 | A | 12/1999 | Yang et al. | |
| 2003/0125135 | A1 | 7/2003 | Iwami et al. | |
| 2003/0144085 | A1 | 7/2003 | Sasaki et al. | |
| 2010/0029894 | A1 | 2/2010 | Warakomski et al. | |
| 2010/0168320 | A1 | 7/2010 | Schwaim et al. | |
| 2013/0053179 | A1 | 2/2013 | Tarao et al. | |
| 2015/0183922 | A1 * | 7/2015 | Nakagawa | C09D 11/102 428/407 |

FOREIGN PATENT DOCUMENTS

| | | |
|---|---|---|
| CN | 1328298 | 7/2007 |
| CN | 100404577 | 7/2008 |
| CN | 101821311 | 9/2010 |
| CN | 101868488 | 10/2010 |
| CN | 102056955 | 5/2011 |
| CN | 103097424 | 5/2013 |
| CN | 104395417 | 3/2015 |
| CN | 104781229 | 7/2015 |
| CN | 105026453 | 11/2015 |
| CN | 105377808 | 3/2016 |
| CN | 105934458 | 9/2016 |
| CN | 110982034 | 4/2020 |
| IN | 108752240 | 11/2018 |
| JP | H10259167 A | 9/1998 |
| JP | 2006504849 A | 2/2006 |
| JP | 2013048806 A | 3/2013 |
| JP | 2013-076076 | 4/2013 |
| TW | 201930260 | 8/2019 |
| WO | 2015016148 A1 | 2/2015 |
| WO | 2015046370 A1 | 4/2015 |
| WO | 2019132491 A1 | 7/2019 |

OTHER PUBLICATIONS

PCT Search Report prepared for PCT Application No. PCT/CN2020/100732, completed Sep. 14, 2020.

Chinese Search Report prepared for Chinese Patent Application No. 201911199670X.

Chinese Office Action prepared for Chinese Patent Application No. 201911199670X.

Kausar, A., et al., "Effect of Nanofiller Dispersion On Morphology, Mechanical and Conducting Properties of Electroactive Shape Memory Poly(Urethane-Urea)/Functional Nanodiamond Composite," 2015, Nanosciences and Catalysis Division, National Centre For Physics.

Xie, Rui, et al., "Polyurethane Elastomers Based on 1,3 and 1,4-Bis(Isocyanatomethyl)cyclohexane." 2009, Journal of Applied Polymer Science, vol. 113, 839-848.

Zhang, Youwe, et al., Preperation of Polythiourethane Optical Resin Based 2, 3-b is [2-mercaptoethyl) thio] -1-propanethiol and 1, 3-bis (isocayanantomethyl) cyclohexane, 2021, Glass Enamel & Ophthalmic Optics.

Seidler, Konstanze, et al., A Structural Reconsideration: Linear Aliphatic or Alicyclic Hard Segments for Biodegradable Thermoplastic Polyurethanes?, 2018, Journal of Polymer Science, DOI: 10.1002/pola.29190, pp. 1-11.

Supplemental Chinese Search Report prepared for Chinese Patent Application No. 201911199670X.

Wang, Guiyou, et al., "Synthesis of ADI/HDI hybrid isocyanurate and its application in polyurethane coating," 2015, J. Coat. Technol. Res., DOI 10.1007/s11998-014-9650-3, pp. 1-11.

* cited by examiner

1,3-BISISOCYANATOMETHYLCYCLOHEXANE COMPOSITION AND OPTICAL RESIN PREPARED THEREFROM

CROSS-REFERENCE TO RELATED APPLICATIONS

This application is a national stage entry under 35 USC § 371 (b) of PCT International Application No. PCT/CN2020/100732, filed Jul. 7, 2020, which the benefit of Chinese Patent Application Serial No. 201911199670.X, filed Nov. 29, 2019. The entire contents of this priority document are incorporated herein by reference, except that in the event of any inconsistent disclosure or definition from the present specification, the disclosure or definition herein shall be deemed to prevail.

TECHNICAL FIELD

The present disclosure relates to the field of isocyanates, and particularly to a 1,3-bis(isocyanatomethyl)cyclohexane composition used for an optical resin.

BACKGROUND

Optical resins are widely used in glass for glasses, airplanes and automobiles, and optical components such as lenses and prisms.

Polyurethane resin is the most important one of optical resins, which are obtained by subjecting polythiol compounds and isocyanate compounds to polymerization reaction. Such optical resin has excellent characteristics such as high refractive index, impact resistance, dyeability and processability. Moreover, due to the relatively high refractive index of polyurethane lens, the lens can be made very thin and more beautiful, which is the development tendency of the lens in the future.

However, in the polymerization process of polyurethane lens, due to the influence of impurities or isomers in the raw material, the resin often has white turbidity, opaque, and optical distortion, causing unqualified lens.

Therefore, it is necessary to control the raw material and process of lens polymerization, mainly to control the isocyanate raw material to reduce the occurrence of white turbidity and optical distortion.

U.S. Pat. No. 5,576,412 discloses that by controlling the hydrolyzable chlorine to less than 300 ppm in isocyanate, a lens resin with less discoloration and high light transmittance can be obtained. Chinese patent CN102516487 discloses that by controlling the water content to 10 ppm to 300 ppm in isocyanate and polythiol, the optical material without striation and white turbidity appearing can be obtained.

SUMMARY

An object of the present disclosure is to provide a 1,3-bis(isocyanatomethyl)cyclohexane composition and an optical resin prepared therefrom. By controlling the contents of 1,4-HXDI and cis- or trans-isomers in a 1,3-HXDI raw material, preferably by further controlling the content of 1-isocyanatomethyl-3-methylcyclohexane, a high-performance optical resin without white turbidity and optical distortion appearing can be obtained.

To achieve the above object, a technical solution provided in the present disclosure is as follows:

a 1,3-bis(isocyanatomethyl)cyclohexane composition is provided by the present disclosure, comprising: based on a weight of 1,3-bis(isocyanatomethyl)cyclohexane (1,3-HXDI),
a) 65 wt % to 95 wt % trans-1,3-bis(isocyanatomethyl)cyclohexane; and
b) greater than 0 and less than or equal to 0.5 wt %, preferably 0.02 wt % to 0.5 wt % of 1,4-bis(isocyanatomethyl)cyclohexane (1,4-HXDI);
the 1,3-bis(isocyanatomethyl)cyclohexane comprises cis-1,3-bis(isocyanatomethyl)cyclohexane and trans-1,3-bis(isocyanatomethyl)cyclohexane.

As a preferred solution, the 1,3-bis(isocyanatomethyl)cyclohexane composition of the present disclosure includes more than 0 and less than or equal to 600 ppm, preferably 0.1 ppm to 600 ppm of 1-isocyanatomethyl-3-methylcyclohexane

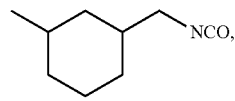

based on the weight of 1,3-bis(isocyanatomethyl)cyclohexane.

A preparation method of the 1,3-bis(isocyanatomethyl)cyclohexane composition of the present disclosure includes the following steps: (1) a salt-forming process, mixing a 1,3-cyclohexyl dimethylamine raw material with hydrogen chloride to prepare 1,3-cyclohexyldimethylamine hydrochloride; (2) an isocyanate-forming process, subjecting the 1,3-cyclohexyldimethylamine hydrochloride and phosgene to an isocyanate-forming reaction, of which a product includes 1,3-bis(isocyanatomethyl)cyclohexane and 1-isocyanatomethyl-3-methylcyclohexane; (3) a purification process, performing purification on the aforementioned product to prepare the 1,3-bis(isocyanatomethyl)cyclohexane composition of the present disclosure.

As a preferred solution, the contents of 1,4-bis(isocyanatomethyl)cyclohexane, cis-1,3-bis(isocyanatomethyl)cyclohexane and trans-1,3-bis(isocyanatomethyl)cyclohexane in the 1,3-bis(isocyanatomethyl)cyclohexane composition can be achieved by controlling the composition of 1,3-cyclohexyldimethylamine raw material; in 1,3-cyclohexyldimethylamine, a proportion of cis- or trans-isomers can be adjusted through a catalyst under hydrogen atmosphere; trans-1,3-cyclohexyldimethylamine has a content of 50 wt % to 95 wt %, and cis-1,3-cyclohexyldimethylamine has a content of 5 wt % to 50 wt %; preferably, trans-1,3-cyclohexyldimethylamine has a content of 65 wt % to 95 wt %, and cis-1,3-cyclohexyldimethylamine has a content of 5 wt % to 35 wt %, based on the weight of 1,3-cyclohexyldimethylamine raw material. Additionally, the proportion of cis- or trans-isomers can also be adjusted through rectification separation in the purification process of 1,3-bis(isocyanatomethyl)cyclohexane composition.

As a preferred solution, a preparation method of the 1,3-cyclohexyldimethylamine raw material includes the following steps: subjecting 1,3-cyclohexyldimethylamine (trans-1,3-cyclohexyl dimethylamine:cis-1,3-cyclohexyldimethylamine=50:50) to an isomerization reaction for 1 h to 4 h, with a ruthenium/alumina catalyst, a hydrogen absolute pressure of 4 MPa to 6 MPa, and a temperature of 200° C. to 220° C.

As a preferred solution, a content of 1-isocyanatomethyl-3-methylcyclohexane is achieved by controlling a rectification condition in the purification process.

The present disclosure also provides an optical resin, which is prepared by polymerizing the 1,3-bis(isocyanatomethyl)cyclohexane composition of the present disclosure and a polythiol compound.

A preparation method of the optical resin includes mixing the isocyanate composition with the polythiol compound and then polymerizing them to obtain the optical resin.

The polythiol compound of the present disclosure includes one or more of aliphatic polythiol, aromatic polythiol, polythiol containing a heterocycle, aliphatic polythiol containing a sulfur atom in addition to mercapto, aromatic polythiol containing a sulfur atom in addition to mercapto, and polythiol containing a sulfur atom in addition to a heterocycle and mercapto.

In a particular preference, the polythiol compound used is at least one selected from the group consisting of 1,2-bis[(2-mercaptoethyl)thio]-3-mercaptopropane, bis(mercaptomethyl)-3,6,9-tri thia-1,11-undecanedithiol, pentaerythritol tetrakis(3-mercaptopropionate), 1,1,3,3-tetrakis (mercaptomethylthio)propane and 2-mercaptoethanol.

Preferably, the preparation method of optical resin is carried out in the presence of a polymerization catalyst; the polymerization catalyst is preferably an organotin compound, for example, dialkyltin halide such as dibutyltin dichloride or dimethyltin dichloride, and dialkyltin dicarboxylate such as dimethyltin diacetate, dibutyltin dioctanoate and dibutyltin dilaurate.

Additionally, according to an object, in the preparation method of the optical resin, various adjuvants are optionally added including a chain extender, crosslinking agent, light stabilizer, ultraviolet absorber, antioxidant, oil-soluble dye, filler, mold release agent and the like.

An optical material formed from polyurethane resin is generally produced by injection molding polymerization, specifically including mixing the polythiol compound and the isocyanate compound, and optionally adding the suitable adjuvant. When necessary, the mixture (polymerizable composition) is defoamed by an appropriate method, and then injected into an injection mold for optical materials, and usually the mixture is gradually heated from a low temperature to a high temperature for polymerization. Then, the optical material is obtained by demolding.

A lens made from the optical resin of the present disclosure.

The polymerization rate of isocyanate and polythiol has a great influence on the lens resin. If the polymerization rate is too fast, the resin will appear optical distortion and bubbles, while if the polymerization rate is two slow, the opaque white turbidity is prone to be introduced to the resin.

The inventor surprisingly found that the contents of 1,4-HXDI content, and cis-1,3-HXDI and trans-1,3-HXDI in 1,3-HXDI have a great influence on the polymerization rate. By controlling the contents of 1,4-HXDI, cis-1,3-HXDI and trans-1,3-HXDI in 1,3-HXDI at a certain level, the lens resin with good transparency and no optical distortion can be obtained.

Additionally, the presence of a micro-amount of 1-isocyanatomethyl-3-methylcyclohexane can make the polymerization reaction more stable, but if the content of 1-isocyanatomethyl-3-methylcyclohexane is too high, due to the reduction of the average number of total functional groups in the composition, the polymerization is not uniform and the polymer structure is affected, easily resulting in optical distortion appearing.

The technical solution of the present disclosure has the following beneficial effects:

In the 1,3-bisisocyanatomethylcyclohexane composition of the present disclosure, on account of that the contents of 1,4-HXDI, trans-1,3-HXDI and 1-isocyanatomethyl-3-methylcyclohexane are in the specific range, the lens obtained from the prepared optical resin has incidence rates less than 2% of both optical distortion and white cloudiness.

DETAILED DESCRIPTION

Figure 1:
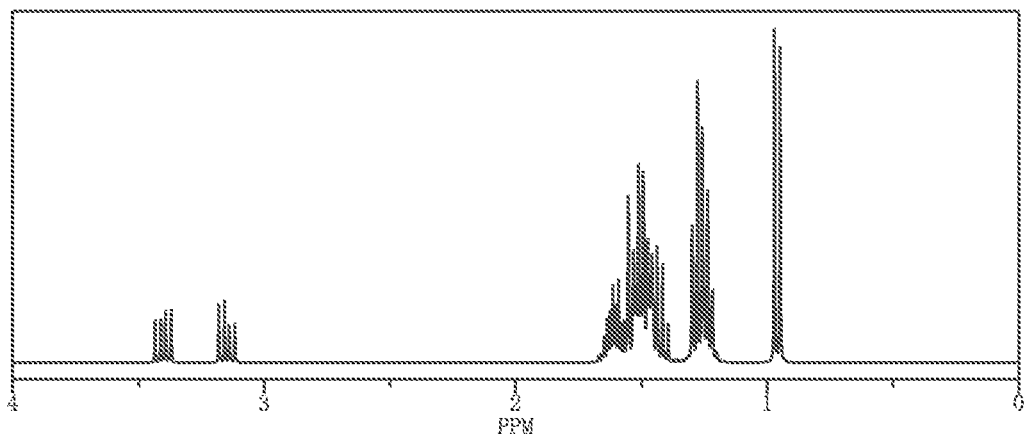
FIG. 1 is a $^1$H NMR spectrum of 1-isocyanatomethyl-3-methyl cyclohexane.
Figure 2:
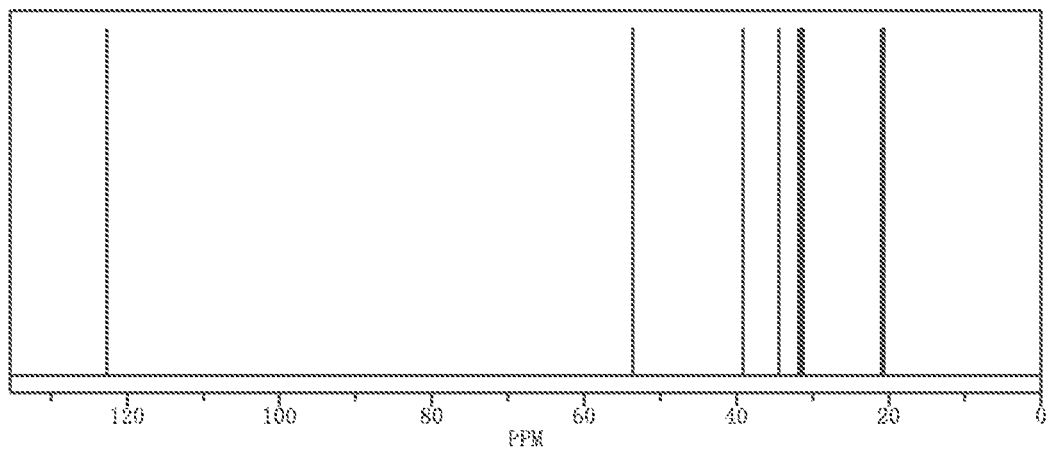
FIG. 2 is a $^{13}$C NMR spectrum of 1-isocyanatomethyl-3-methylcyclohexane.

Although the method provided by the present disclosure is further illustrated below through embodiments, the present disclosure is not limited to the listed embodiments, and further comprises any other common modifications within the scope of the claims of the present disclosure.

The isomer content and micro-impurities of the present disclosure were determined by Agilent 7890 Gas Chromatography. Gas chromatography analysis parameters are as follows: (1) column DB-5 (30 m×0.25 mm×0.25 μm); (2) injection volume: 0.5 μL; (3) split ratio: 1/30; (4) injection port temperature: 260° C.; (5) flow rate in the column: 1.5 mL/min; (6) programed temperature: holding 100° C. for 1 min, warming up to 280° C. at 10° C./min and holding for 20 min; (7) FID detector temperature: 280° C.; (8) hydrogen flow rate: 40 mL/min, and air flow rate: 400 ml/min.

The viscosity test of the present disclosure was performed on a Brookfield rotor viscometer.

The nuclear magnetic analysis of the present disclosure was performed on Bruker 400 MHz.

Incidence rate of optical distortion: optical distortion refers to a phenomenon that the local refractive index is different from the surrounding normal refractive index, one reason of which is the different resin compositions. Under a high-pressure mercury lamp, 100 lenses were visually observed, and the lens confirmed to show striation was judged as a lens with optical distortion, and the incidence rate of optical distortion was calculated.

Incidence rate of white turbidity: under a high-pressure mercury lamp, 100 lenses were visually observed, and the lens confirmed to be turbid was judged as a lens with white turbidity, and the incidence rate of white turbidity was calculated.

Polymerization rate: the time when the polymerizability composition was prepared was regarded as 0 hour, and the viscosity after 5 hours was regarded as an index to evaluate.

Isomerization of 1,3-cyclohexyldimethylamine

To a stainless steel reactor equipped with a stirrer, thermometer and gas-feeding tube, 1000 g of 1,3-cyclohexyldimethylamine (Tokyo Chemical, trans-1,3-cyclohexyldimethylamine:cis-1,3-cyclohexyldimethylamine=50:50), 16 g ruthenium/alumina catalyst (Sigma Aldrich) and 1000 g heptane were added, and the reactor was displaced with hydrogen three times. With stirring of 500 rpm, temperature of 210° C. and hydrogen absolute pressure of 5 MPa, the mixture reacted for 1 h to 4 h, and cooled to the room temperature after the reaction was finished, and subjected to filtration to remove the catalyst. The solvent was removed, and by rectification separation the 1,3-cyclohexyldimethylamine raw material was obtained. According to the different reaction time, the following 1,3-cyclohexyldimethylamine raw materials were obtained respectively.

TABLE 1

Condition and result of the isomerization of 1,3-cyclohexyldimethylamine

| 1,3-cyclohexyldimethylamine raw material | Reaction time/h | Content of trans-1,3-cyclohexyldimethylamine/% |
|---|---|---|
| (A) | 1 | 65 |
| (B) | 1.5 | 75 |
| (C) | 2 | 80 |
| (D) | 2.5 | 85 |
| (E) | 3 | 90 |
| (F) | 3.5 | 95 |

Structure Determination of 1-isocyanatomethyl-3-methylcyclohexane

In a stainless steel reactor, 1420 g of 1,3-cyclohexyldimethylamine raw material (B) was dissolved in 12240 g of o-dichlorobenzene, and hydrogen chloride gas was introduced at a rate of 800 L/h. The salt-forming reaction was performed, controlling the temperature to less than 30° C. After the salt-forming was finished, a milk-white viscous substance was obtained. The temperature was raised to 150° C., and phosgene was introduced at a rate of 500 L/h to perform the phosgenation reaction, and the unreacted phosgene was collected through condensation and then introduced to the alkaline cleaning system for elimination. When the reaction liquid became clarified, the phosgenation reaction was completed, and nitrogen was introduced to drive out the unreacted phosgene, and after subsequent solvent removal, the crude product of 1,3-HXDI was obtained.

500 g of 1,3-HXDI crude product was subjected to heat treatment at 190° C. for 2 h, and the obtained sample was to be rectification separated. Then the substance was fed from the middle of rectification column. The operating pressure in top of the column was 100 pa, and the temperature of the reboiler at bottom of the column was 140° C. At this time, the temperature in top of the column was 110° C., and the reflux ratio was controlled at 20:1. After reaching a steady state, 25 g of light component was collected from the top of the column Through gas chromatography analysis, the light component contained 99.0% impurity of 1-isocyanatomethyl-3-methylcyclohexane, and the NMR data is: $^1$H NMR (400 MHz, DMSO) δ 3.40-3.36 (m, 1H), 3.19-3.15 (m, 1H), 1.61-1.40 (m, 7H), 1.27-1.24 (m, 3H), 0.95-0.97 (d, 3H); $^{13}$C NMR (100 MHz, DMSO): δ 122.7, 53.6, 39.1, 34.4, 31.8, 31.5, 31.2, 21.0, 20.6.

Example 1

In a stainless steel reactor, 1420 g of 1,3-cyclohexyldimethylamine raw material (B) was dissolved in 12240 g of o-dichlorobenzene, and hydrogen chloride gas was introduced at a rate of 800 L/h. The salt-forming reaction was performed, controlling the temperature to less than 30° C. After the salt-forming was finished, a milk-white viscous substance was obtained. The temperature was raised to 150° C., and phosgene was introduced at a rate of 500 L/h to perform the phosgenation reaction, and the unreacted phosgene was collected through condensation and then introduced to the alkaline cleaning system for elimination. When the reaction liquid became clarified, the phosgenation reaction was completed, and nitrogen was introduced to drive out the unreacted phosgene, and after subsequent solvent removal, the crude product of 1,3-HXDI was obtained.

Then, a glass rectification column, which had an inner diameter of 20 mm and a length of 1500 mm and was filled with structured packing, was used to performed rectification on the obtained crude 1,3-HXDI. The crude 1,3-HXDI was preheated to 120° C. with a preheater, and then fed from the middle of the rectification column. The operating pressure in the top of the column is 100 pa, and the temperature of the reboiler at bottom of the column was 145° C. At this time, the temperature in top of the column was 115° C., and the reflux ratio was controlled at 30:1. After reaching a steady state, 1,3-HXDI composition was collected from the top of the column. Through gas chromatography analysis, 1,4-HXDI had a content of 0.1 wt % in the composition, and 1-isocyanatomethyl-3-methylcyclohexane had a content of 10 ppm, which were calculated based on the weight of 1,3-HXDI in the composition; and the trans isomer accounted for 75% in 1,3-HXDI.

At 25° C., 53.7 g of the 1,3-HXDI composition prepared above, 0.075 g of dibutyltin dichloride as a catalyst, 0.10 g of acid-form phosphate (Stepan company, trade name Zelec UN), 0.05 g of ultraviolet absorber (Kyodo Co., Ltd., trade name BioSorb 583) were mixed and dissolved. Moreover, 48 g of 1,2-bis[(2-mercaptoethyl)thio]-3-mercaptopropane (Chambroad Chemical. Co., Ltd.) was added and mixed to form a mixed uniform liquid (polymerizable composition). The time when the mixed uniform liquid was prepared was regarded as 0 hours, and the viscosity after 5 hours was measured.

At 25° C., 53.7 g of 1,3-HXDI composition, 0.075 part (namely 0.075 g) of dibutyltin dichloride as catalyst, 0.10 part (namely 0.10 g) of acid-form phosphate (Stepan company, trade name Zelec UN), 0.05 part (namely 0.05 g) of ultraviolet absorber (Kyodo Co., Ltd., trade name BioSorb 583) were mixed and dissolved. Moreover, 48 g (namely 48 g) of 1,2-bis[(2-mercapto ethyl)thio]-3-mercaptopropane (Chambroad Chemical. Co., Ltd.) was added and mixed to form a mixed uniform liquid (polymerizable composition). After defoamed under 600 Pa for 1 hour, the mixed uniform liquid was filtrated by a 1µ PTFE (polytetrafluoroethylene) filter. Then, the liquid was injected into an injection mold for lens, which was consisted of a 4D glass mold with a diameter of 75 mm and adhesive tapes. The injection mold was placed in an oven, and kept at 40° C. for 2 hours, heated to 50° C. in 4 hours and kept for 2 hours, and heated to 60° C. in 3 hours and kept for 2 hours. Then, the mold was further heated to 70° C. in 3 hours and kept for 2 hours, and heated to 100° C. in 3 hours, and further heated to 130° C. in 1 hour and kept for 2 hours. After the polymerization is completed, the injection mold was taken out from the oven and demolded to obtain a lens. The obtained lens was then annealed at 120° C. for 3 hours. According to the same method, 100 lenses were produced, and the incidence of glass wave (namely incidence rate of optical deformation) and the incidence of white turbidity were calculated. The results are shown in Table 2.

Examples 2-6 and Comparative Examples 1-5

By changing the 1,3-cyclohexyldimethylamine raw material and regulating different reflux ratios, the samples with different indexes were obtained, as shown below in Table 2.

TABLE 2

Condition and result of Examples 1-6 and Comparative Examples 1-5

| No. | | 1,3-cyclohexyl-dimethylamine raw material | reflux ratio | trans-1,3-HXDI content/% | 1,4-HXDI content/% | 1-isocyanatomethyl-3-methylcyclohexane content/ppm | Viscosity after 5 h/cp | Incidence rate of optical distortion | Incidence rate of white turbidity |
|---|---|---|---|---|---|---|---|---|---|
| Example | 1 | (B) | 30:1 | 75 | 0.1 | 10 | 280 | 0 | 0 |
|  | 2 | (C) | 20:1 | 80 | 0.2 | 50 | 300 | 0 | 1 |
|  | 3 | (D) | 10:1 | 85 | 0.3 | 150 | 350 | 1 | 0 |
|  | 4 | (E) | 8:1 | 90 | 0.4 | 400 | 360 | 0 | 1 |
|  | 5 | (F) | 5:1 | 95 | 0.5 | 600 | 380 | 1 | 1 |
|  | 6 | (A) | 40:1 | 65 | 0.02 | 0.1 | 270 | 0 | 0 |
| Comparative example | 1 | (F) | 50:1 | 96 | 0.2 | 50 | 470 | 4 | 2 |
|  | 2 | (B) | 8:1 | 75 | 0.6 | 10 | 450 | 5 | 3 |
|  | 3 | (B) | 1:1 | 75 | 0.1 | 700 | 200 | 6 | 4 |
|  | 4 | (A) | 10:1 | 60 | 0.1 | 10 | 210 | 3 | 5 |
|  | 5 | (B) | 50:1 | 75 | 0.1 | 0 | 450 | 5 | 4 |

"Trans-1,3-HXDI content/%" in Table 2 refers to the content of trans-1,3-HXDI based on the weight of 1,3-HXDI.

"1,4-HXDI content/%" refers to the content of 1,4-HXDI based on the weight of 1,3-HXDI.

"1-isocyanatomethyl-3-methylcyclohexane content/ppm" refers to the content of 1-isocyanatomethyl-3-methylcyclohexane based on the weight of 1,3-HXDI.

What is claimed is:

1. A 1,3-bis(isocyanatomethyl)cyclohexane composition, comprising: based on a weight of 1,3-bis(isocyanatomethyl)cyclohexane,
   a) 65 wt % to 95 wt % of trans-1,3-bis(isocyanatomethyl)cyclohexane; and
   b) greater than 0 and less than or equal to 0.5 wt % of 1,4-bis(isocyanatomethyl)cyclohexane;
   wherein the 1,3-bis(isocyanatomethyl)cyclohexane comprises cis-1,3-bis(isocyanatomethyl)cyclohexane and trans-1,3-bis(isocyanatomethyl)cyclohexane;
   wherein the 1,3-bis(isocyanatomethyl)cyclohexane composition comprises more than 0 and less than or equal to 600 ppm of 1-isocyanatomethyl-3-methylcyclohexane, based on the weight of 1,3-bis(isocyanatomethyl)cyclohexane.

2. The 1,3-bis(isocyanatomethyl)cyclohexane composition according to claim 1, wherein a preparation method of the composition comprises the following steps: (1) a salt-forming process, mixing a 1,3-cyclohexyldimethylamine raw material with hydrogen chloride to prepare 1,3-cyclohexyldimethylamine hydrochloride; (2) an isocyanate-forming process, subjecting the 1,3-cyclohexyldimethylamine hydrochloride and phosgene to an isocyanate-forming reaction, of which a product includes 1,3-bis(isocyanatomethyl)cyclohexane and 1-isocyanatomethyl-3-methylcyclohexane; and (3) a purification process, performing purification on the product of step (2) to prepare the 1,3-bis(isocyanatomethyl)cyclohexane composition.

3. The 1,3-bis(isocyanatomethyl)cyclohexane composition according to claim 2, wherein in the 1,3-cyclohexyldimethylamine raw material, trans-1,3-cyclohexyldimethylamine has a content of 50 wt % to 95 wt %, and cis-1,3-cyclohexyldimethylamine has a content of 5 wt % to 50 wt %, based on the weight of 1,3-cyclohexyldimethylamine raw material.

4. The 1,3-bis(isocyanatomethyl)cyclohexane composition according to claim 2, wherein a preparation method of the 1,3-cyclohexyldimethylamine raw material comprises the following step: subjecting 1,3-cyclohexyldimethylamine (trans-1,3-cyclohexyldimethylamine: cis-1,3-cyclohexyldimethylamine=50:50) to a isomerization reaction for 1 h to 4 h, with a ruthenium/alumina catalyst, a hydrogen absolute pressure of 4 MPa to 6 MPa, and a temperature of 200° C. to 220° C.

5. An optical resin, which is prepared by polymerizing the 1,3-bis(isocyanatomethyl)cyclohexane composition according to claim 1 and a polythiol compound raw material.

6. The optical resin according to claim 5, wherein the polythiol compound comprises one or more of aliphatic polythiol, aromatic polythiol, polythiol containing a heterocycle, aliphatic polythiol containing a sulfur atom in addition to mercapto, aromatic polythiol containing a sulfur atom in addition to mercapto, and polythiol containing a sulfur atom in addition to a heterocycle and mercapto.

7. The optical resin according to claim 6, wherein the polythiol compound comprises one or more of 1,2-bis[(2-mercaptoethyl)thio]-3-mercaptopropane, bis(mercaptomethyl)-3,6,9-trithia-1,11-undecanedithiol, pentaerythritol tetrakis(3-mercaptopropionate), 1,1,3,3-tetrakis(mercapto methylthio)propane and 2-mercaptoethanol.

8. A lens, which is prepared from the optical resin according to claim 5.

9. The 1,3-bis(isocyanatomethyl)cyclohexane composition according to claim 1, comprising: based on a weight of 1,3-bis(isocyanatomethyl)cyclohexane,
   a) 65 wt % to 95 wt % of trans-1,3-bis(isocyanatomethyl)cyclohexane; and
   b) 0.02 wt % to 0.5 wt % of 1,4-bis(isocyanatomethyl)cyclohexane.

10. The 1,3-bis(isocyanatomethyl)cyclohexane composition according to claim 1, wherein the 1,3-bis(isocyanatomethyl)cyclohexane composition comprises 0.1 ppm to 600 ppm of 1-isocyanatomethyl-3-methylcyclohexane, based on the weight of 1,3-bis(isocyanatomethyl)cyclohexane.

11. The 1,3-bis(isocyanatomethyl)cyclohexane composition according to claim 3, wherein in the 1,3-cyclohexyldimethylamine raw material, trans-1,3-cyclohexyldimethylamine has a content of 65 wt % to 95 wt %, and cis-1,3-cyclohexyldimethylamine has a content of 5 wt % to 35 wt %, based on the weight of 1,3-cyclohexyldimethylamine raw material.

* * * * *